United States Patent [19]

Sandbank

[11] Patent Number: 5,035,687
[45] Date of Patent: Jul. 30, 1991

[54] ADHESIVE DRESSINGS

[75] Inventor: Barry M. Sandbank, Bishop's Stortford, United Kingdom

[73] Assignee: Smith & Nephew plc, England

[21] Appl. No.: 271,520

[22] Filed: Nov. 15, 1988

[30] Foreign Application Priority Data

Nov. 16, 1987 [GB] United Kingdom ............... 8726777

[51] Int. Cl.$^5$ .................. A61F 13/02; A61M 25/02
[52] U.S. Cl. ................................ 604/180; 604/307;
128/155; 128/DIG. 26
[58] Field of Search ....... 128/155, 156, 169, DIG. 26;
604/180, 304, 307; 206/440, 441

[56] References Cited

U.S. PATENT DOCUMENTS

| | | | |
|---|---|---|---|
| 1,852,040 | 4/1932 | Blank | 206/440 |
| 2,969,144 | 1/1961 | Zackheim | 128/155 |
| 3,119,495 | 1/1964 | Pratt | 206/440 |
| 4,265,234 | 5/1981 | Schaar | 206/441 |
| 4,607,633 | 8/1986 | Lauritzen | 128/156 |
| 4,643,180 | 2/1987 | Feld et al. | 128/156 |
| 4,781,293 | 11/1988 | Johns | 128/156 |
| 4,815,457 | 3/1989 | Mazars et al. | 128/155 |

FOREIGN PATENT DOCUMENTS

| | | |
|---|---|---|
| 0035399 | 9/1981 | European Pat. Off. . |
| 0050035 | 4/1982 | European Pat. Off. . |
| 0051935 | 5/1982 | European Pat. Off. . |
| 0091800 | 10/1983 | European Pat. Off. . |
| 0123465 | 10/1984 | European Pat. Off. . |
| 0178740 | 4/1986 | European Pat. Off. . |
| 1254818 | 11/1967 | Fed. Rep. of Germany ...... 128/155 |
| 8600220 | 1/1986 | PCT Int'l Appl. ............... 128/155 |
| 1280631 | 7/1972 | United Kingdom . |
| 1531715 | 11/1978 | United Kingdom . |
| 2157955 | 11/1985 | United Kingdom . |
| 2202150 | 9/1988 | United Kingdom ............... 128/156 |

*Primary Examiner*—Stephen C. Pellegrino
*Assistant Examiner*—Ralph A. Lewis
*Attorney, Agent, or Firm*—Rosenman & Colin

[57] ABSTRACT

An adhesive dressing comprises a backing layer having over one surface a pressure sensitive adhesive layer. A removable protector covers the adhesive layer and a handling means is present at one edge of the backing layer. The dressing has a fold in a direction substantially parallel to the handling means so that the backing layer is on the outside of the fold. The portion of the dressing beyond the fold is releasably attached to the portion of the dressing before the fold preferably by means of a double-sided tape. In use the protector may be peeled from the adhesive layer up to the fold when peeling will stop. The protector and handling means may be used to position the dressing on the skin. Application of a further force peels the protector from the rest of the adhesive surface. The dressings are for use as I.V. dressings.

36 Claims, 2 Drawing Sheets

ADHESIVE DRESSINGS

BACKGROUND OF THE INVENTION

The present invention relates to adhesive dressings for human use. More specifically this invention relates to dressings which comprise a backing layer coated on one surface thereof with a pressure sensitive adhesive layer and which are provided with a protector over the adhesive layer.

DESCRIPTION OF THE PRIOR ART

One type of adhesive dressing which has been successfully used as a dressing for skin traumas, surgical incisions and for covering catheter sites comprises a backing layer of a moisture vapor permeable, thin, flexible, elastomeric material coated on one surface with an adhesive. These dressings maybe presented for use with a protector covering the adhesive layer and with a handling means at one edge or at a pair of opposed edges. Application of such dressings is usually achieved by removing the protector from the adhesive layer and placing the dressing on the skin using the handling means to stabilize the dressing during application. One disadvantage which sometimes is observed with these flexible dressings is that during application they may crease or pucker or otherwise self-adhere and the dressing must be discarded. One approach to seek to minimize the incidence of this wasteful occurence has been to place a fold across the dressing to provide extra stability during application. This has been used successfully with a catheter dressing available as OpSite IV Dressing (OpSite is a Trade Mark). However, in this case if the protector is peeled strongly from the adhesive layer, it is possible to accidentally peel the protector beyond the fold and so lose the stabilising influence provided by the fold. It has now been found that by releasably attaching a portion of the dressing beyond the fold to a portion of the dressing before the fold, then when the protector is peeled from the adhesive layer its progress is stopped at the fold so that the dressing is stabilised against creasing. The part of the dressing with exposed adhesive may then be applied to the skin. Subsequent application of a higher peeling force peels the protector past the fold and separates the parts of the protector attached to each other. The remainder of the dressing may then be smoothed into place as the protector is finally removed. The presence of the fold also serves as a reference point to a nurse when applying the dressing to a catheter site so that the dressing maybe accurately positioned with the minimum of manipulation.

SUMMARY OF THE INVENTION

Accordingly the present invention provides an adhesive dressing comprising a backing layer having over a surface thereof a pressure sensitive adhesive layer, a removable protector which covers the adhesive layer and a handling means at one edge of the backing layer and in which the dressing has a fold in a direction parallel to the handling means with the backing layer on the outside of the fold and in which a portion of the dressing beyond the fold is releasably attached to a portion of the dressing before the fold.

DESCRIPTION OF THE PREFERRED EMBODIMENT

Aptly the fold is positioned away from the edge of the dressing and is suitably within the second half of the dressing when measured from the edge attached to the handling means. The fold is suitably within 40 to 90% of the distance across the dressing measured from the edge of the dressing attached to the handling means, more suitably is within 50 to 80% of the distance across the dressing and preferably is within 60 to 75% of the distance across the dressing. The direction of the fold is suitably substantially parallel to the handling means. The fold is made in such a way that the backing layer is on the outside of the fold and the protector is on the inside of the fold.

It is clear therefore that the dressing may be considered as having two portions, one portion beyond the fold and a portion before the fold which carries the handling means. These two portions are releasably attached to each other in such a way that one part of the protector is attached to another part of the protector.

Aptly the force required to separate the two portions may be such that it is greater than the peel force required to separate the protector from the adhesive layer in the portion of the dressing before the fold so that the peel will come to a stop at the fold. An extra force will be required to peel the protector past the fold as the end of the protector is now also being separated from the adhesive surface of the means which releasably attaches the two portions of the dressing together. The force required to separate the two portions should be low enough to permit separation as the protector is peeled past the fold without affecting the dressing. It is preferred that separation of the two portions of the protector is achieved by the application of a peel force rather than a shear force, since a shear force would normally be greater and could be so large as to affect the stability of the dressing during application. The dressings of the present invention may be constructed so that a peel force is required to separate the portions of the protector.

The method of attachment of the two portions of the protector includes a tape which has a coating of adhesive on either side or a tape coated on only one surface with adhesive which is folded or other means which may fail either adhesively or cohesively under an applied force, for example, an adhesive strip or a semisolid such as a grease. Suitably the attachment is made at the edge of the portion beyond the fold. Preferably the method of attachment is by means of a double sided tape. Aptly the tape may be a paper tape coated on both sides with a pressure sensitive adhesive such as an acrylate ester adhesive or a vinyl ether adhesive.

Aptly the protector extends beyond the edges of the adhesive coated backing layer on two opposite edges, one of which carries the handling means. When the attachment is by means of a double sided tape or adhesive strip, it is advantageous to fold the extended portion of the protector back so that its release surface contacts one adhesive surface of the double-sided tape or adhesive strip. The separation is therefore caused to occur by the preferred peel force rather than a shear force. Alternatively a double-sided release paper may be used with a weak adhesive on a double-sided tape or on a folded single-sided adhesive tape or a simple strip of adhesive.

However, the skilled worker will appreciate that by choosing adhesives of varying aggressiveness and using various double and single-sided release coated protectors, various configurations of adhesive tape and release paper may be prepared which are within the scope of the invention and perform as herein described.

The handling means may be an adhesive-free strip of the backing layer but is preferably a strip of material applied to the non-adhesive surface of the backing layer. The strip of material may or may not be covered by a layer of adhesive but it is preferred if an exposable adhesive surface which is coated with adhesive is present on the handling means.

Suitable strip materials for use as handling means in the invention include those disclosed in the United Kingdom Patent No. 2157955 for the handles of the adhesive dressings described therein.

A favored strip material comprises an net. Preferred nets include those described in British Patent No. 1531715.

The adhesives which may be present on the handling means are favorably those described hereinafter in relation to the adhesive used in the dressings of the invention.

The backing layer suitably comprises any one of the flexible polymer films conventionally used for surgical or wound dressings. The film may be formed from a material which is suitably of a synthetic polymer and most preferably is a film of elastomer. Preferably the flexible film is moisture vapor permeable and bacteria proof. In addition it is most convenient to employ a transparent material. Favored moisture vapor permeable, liquid water impermeable flexible films will have a moisture vapor transmission rate of at least 300 $gm^{-2} 24 H^{-1}$ at 37° C. at a relative humidity difference of 100% to 10%, more suitably at least 400 $gm^{-2} 24 h^{-1}$, preferably at least 500 $gm^{-2} 24 h^{-1}$ and most preferably at least 700 $gm^{-2} 24 h^{-1}$. Moisture vapor transmission rates are measured by the Payne Cup Method.

Suitable backing layers for use in the invention are described in British Patent No. 1280631 and European Patent No. 51935 and European Patent Application No. 178740. Favored backing layers include those formed from a polyether or polyester polyurethane. Suitable polyether polyurethanes are described in U.S. Pat. No. 2,899,411, and suitable polyester polyurethanes are described in U.S. Pat. No. 2,871,218. Suitable polyether and polyester polyurethanes include those known as Estanes (Trade mark, available from B. F. Goodrich Corp). Preferred polyurethanes are available as Estanes 5701, 5702, 5703, 5714F and 580201. A second particularly favored backing layer may be formed from an elastomeric polyether polyester. Preferred polyether polyesters include Hytrel 4056 (Trade mark, available from E. I. du pont de Nemours & Co). A third favored backing layer may be formed from an elastomeric polyamide-polyether polymer. Preferred polyamide-polyether include Pebax 4011 RN (Trade mark).

Suitably the thickness of the backing layer used in the invention will be from 9 to 80 μm, more suitably 15 to 50 μm and preferably 20 to 40 μm for example 25 μm, 30 μm or 35 μm.

Further suitable backing layers which may be used in the invention are described in European Patent Application No. 91800 and European Patent Application No. 123465.

A particularly preferred adhesive dressing has a backing layer formed from a hydrophilic polyurethane as is for example described in European Patent No. 50035.

The adhesive layer used in the dressings of the present invention may be a continuous spread or a non-continuous spread, for example pattern spread, a microporous layer or a porous layer.

Suitably the adhesive layer may be 15 to 65 μm thick, preferably is 20 to 40 μm thick, for example 25, 30 or 35 μm thick. Such adhesive layers may generally have a weight of adhesive per unit area of 10 to 75 $gm^{-2}$, more usually 15 to 65 $gm^{-2}$ and preferably 2 to 40 $gm^{-1}$.

Suitable adhesives include those which are described in British Patent No. 1280631 and European Patent Applications Nos 51935, 35399. Preferably, the adhesive is a polyvinyl ether adhesive such as polyvinyl ethyl ether adhesive or an acrylate adhesive such as an acrylic ester adhesive. Examples of the latter include acrylate ester copolymers which contain hydrophilic groups, for example a copolymer of 47 parts by weight butyl acrylate, 47 parts by weight 2-ethylhexyl acrylate and 6 parts by weight acrylic acid.

If the adhesive layer is a continuous spread then it is prepared from a material which when spread on the backing layer will allow the adhesive coated material to have a moisture vapor transmission rate (mvtr) of at least 300 $gm^{-2} 24 h^{-1}$ at 37° C. and 100% to 10% relative humidity when measured by the Payne Cup Method, more favorably the mvtr will be at least 400 $gm^{-2} 24 h^{-1}$, more favorably at least 500 $gm^{-2} 24 h^{-1}$ and preferably at least 700 $gm^{-2} 24 h^{-1}$.

Suitable protectors may be formed from silicone release coated papers and plastics coated papers and release coated films such as silicone coated polyethylene. The protectors employed in the present invention may have a release coat on one or both surfaces. A favored release protector is a single-sided silicone release/polyethylene coated paper known as Steralease No. 15 (Trade mark, available from Sterling Coated Paper Limited).

The backing layer and/or the adhesive layer can be a carrier for a medicament such as topical medicament for the treatment of wounds or dermatological disorder. Such a medicament, however, is preferably provided on or within the adhesive layer of the dressing.

Suitable topical medicament for use in the invention includes topical antibacterials for example chlorhexidine salts such as chlorhexidine gluconate and chlorhexidine diacetate, silver salts such as silver sulphadiazine, iodophors, polymeric biguanides such as polyhexamethylene biguanide hydrochloride, and topical viricides such as acyclovir.

The dressings of the present invention may be prepared by casting or extruding the backing layer onto a support film, usually the non-release surface of a conventional release paper or polymer. The adhesive layer may be formed by casting or transfer coating an adhesive onto the surface of the backing layer. The adhesive surface of the backing layer may then be transferred onto the release surface of the support film in a conventional manner. The support means may be adapted to extend beyond the edges of the adhesive coated backing layer on two opposite sides or the adhesive coated polymer may be trimmed to achieve the same result. The handling means which may be formed as an adhesive strip on a release paper may be then attached to one edge of the backing layer by temporarily separating the adhesive strip from its release paper, adhering one edge to the backing layer and re-applying the release paper to the exposed adhesive area of the adhesive strip. The extended portion of the protector at the opposite edge to the handling means may be folded so that it lies adjacent to the rest of the protector. A strip of double-sided adhesive tape or an adhesive strip may be placed on the protector in a direction parallel to the handling means. The dressing is then folded to bring the release surface of the extended portion of the protector into contact with the exposed adhesive surface. The strip so formed may be cut into dressings of the appropriate shape and size. The dressings may be packaged into paper pouches and sealed and sterilized in a conventional manner. Alternatively if a double sided release protector is used the second fold in the protector may be omitted.

The adhesive wound dressing of the invention will usually have a rectangular shape. Suitable wound dressings usually have a size of 5 cm×5 cm to 60 cm×100 cm for example 8 cm×8 cm, 10 cm×10 cm, 10 cm×15 cm, 15 cm×15 cm, 20 cm×20 cm.

The flexible film adhesive coated dressings of the invention include wound dressings for example suitable for the treatment of cuts, ulcers, burns, abrasions or dermatological disorders, surgical drapes and catheter fixing dressings. The dressings may be of small, large or medium size. The dressings of the invention, however, are highly suitable for small dressings such as wound dressings, dressings for treating dermatological disorders and dressings for holding indwelling cannula in place.

The adhesive dressing of the invention is preferably sterile. The adhesive dressing of the invention is advantageously provided within a bacteria proof pack such as a sealed aluminium foil or paper/plastics film pouch. Sterilization of the dressing can be carried out by a conventional sterilizing method such as ethylene oxide, electron or gamma radiation.

The present invention also provides a method of treating a patient by applying thereto an adhesive dressing as described hereinbefore.

The present invention also provides a method of retaining an indwelling catheter on the body of a patient by positioning over the catheter a dressing of the present invention which method comprises peeling the protector from the adhesive layer on the dressing upto the fold, applying the adhesive surface to the skin surrounding the catheter and the peeling off the remainder of the protector.

In use the sterile dressing is removed from the pouch, the handling means is grasped and the protector peeled from the adhesive layer upto the fold when the peel is stopped. The dressing may then be positioned over an indwelling catheter and the part of the dressing with exposed adhesive adhered to the skin of the patient and to the catheter. The protector is then peeled past the fold by applying sufficient peel force to unfold the dressing by separating the attachment of the two parts of the dressing. The remainder of the dressing may be smoothed into place on the skin and the protector discarded.

Preferred embodiments of the adhesive dressings of the present invention will be described by way of example only and with reference to the drawings in which,

BRIEF DESCRIPTION OF THE FIGURES

The adhesive dressing (1) shown in FIG. 1 comprises a backing layer (2) formed from a polyurethane film approximately 25 μm in thickness coated on one surface with a pressure sensitive adhesive layer (3) formed from a polyacrylate ester copolymer adhesive coated at a weight per unit area of 30 gsm. A protector (4) covers the adhesive layer (3). The protector (4) is a conventional release paper with the adhesive contacting surface coated with a silicone compound. One edge margin of the backing layer (2) is attached to a handling means (5) comprising an adhesive strip (6), the exposed adhesive surface of which is covered by a silicone release coated paper (7). The dressing (1) is folded lengthwise that is parallel to the direction of the handling means (5) at a point about two-thirds of the distance from the handling means (5) across the dressing. The fold (8) is made so that the backing layer (2) is on the outside of the fold (8). In FIG. 1 the folded portion (9) is releasably attached to the remainder of the dressing at its edge margin by means of a double sided adhesive tape (10). The protector (4) has been extended beyond the edge of the dressing (1) so that when the extended portion is folded as shown its release coated surface may be brought into contact with one exposed surface of the double sided tape (10). The size of the double sided tape has been exaggerated for the sake of clarity, in practice the fold is a sharp fold and the dressing is essentially flat.

Figure 1:
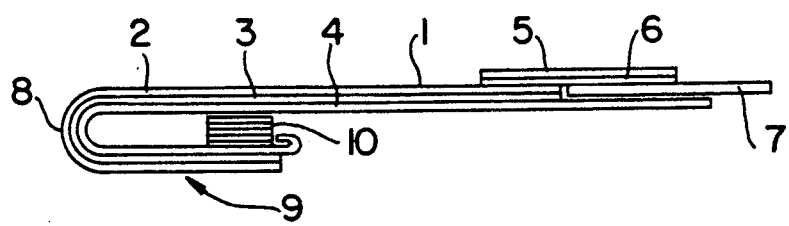
FIG. 1 shows a cross-section through one embodiment of an adhesive dressing according to the invention.

In use the handling means (5) is grasped and the protector (4) is peeled from adhesive layer (3) until the fold (8) is reached when the peeling is stopped. The exposed adhesive portion may be adhered to the skin. Once adhered then the remainder of the adhesive layer (3) may be exposed and adhered to the skin. The adhesive handling means (5) may be torn from the dressing or the release paper (7) may be removed from the handling means (5) which is then adhered to the skin.

Figure 2:
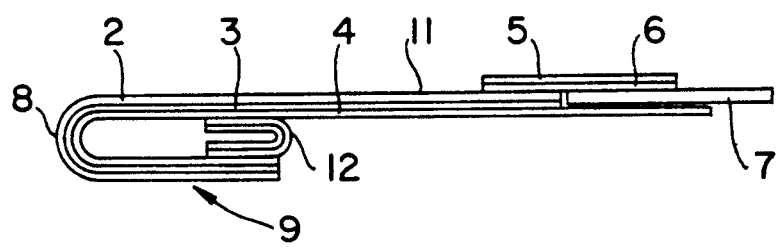
FIG. 2 shows a cross-section through a second embodiment of an adhesive dressing according to the invention.

The adhesive dressing (11) shown in FIG. 2 is similar to that of FIG. 1 except that the folded portion (9) is attached to the remainder of the dressing by means of a folded adhesive strip (12). This may require that the protector (7) comprises a double sided release paper that is a paper which has a release coat in each surface. The openness of the folded adhesive strip has been exaggerated for the sake of clarity, normally the fold (9) would be a sharp fold and the two parts of the folded adhesive tape would lie in contact with each other.

Figure 3:
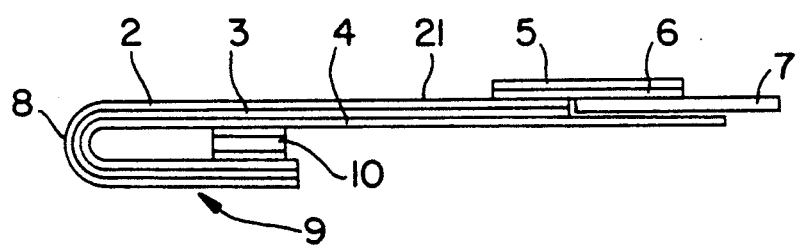
FIG. 3 shows a cross-section through a third embodiment of an adhesive dressing according to the invention.

The adhesive dressing (21) shown in FIG. 3 is similar to that described in FIG. 1 except that the protector (4) has a release coating on either side so that there is no need to fold the protector as in FIG. 1.

Figure 4:
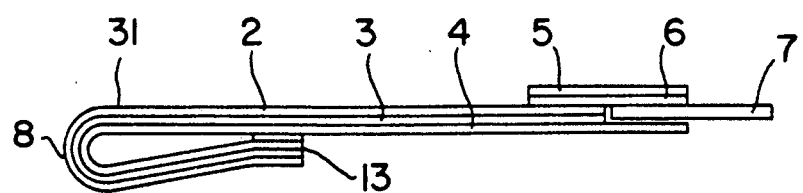
FIG. 4 shows a cross-section through a fourth embodiment of an adhesive dressing according to the invention.
Figure 5:
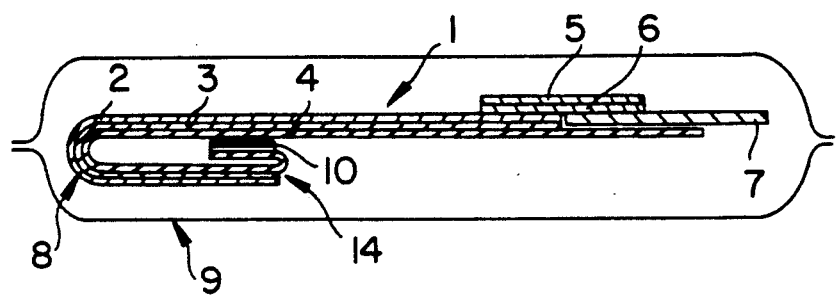
Figure 6:
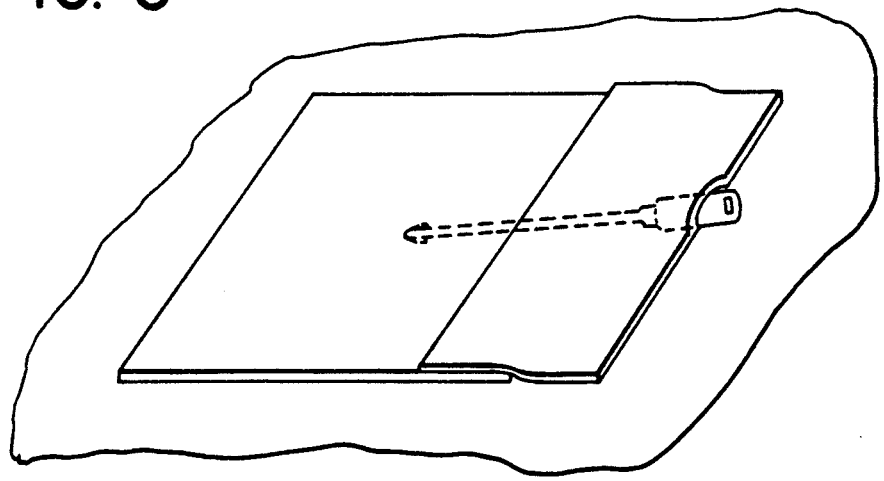

The adhesive dressing (31) shown in FIG. 4 is similar in construction to the dressing described in FIG. 1 except that the protector (4) has a release coating on either side and the attachment means (13) is a strip of adhesive.

I claim:

1. An adhesive dressing comprising a backing layer having over a surface thereof a pressure sensitive adhesive layer, a removable protector having a release coated surface which covers the adhesive layer and handling means at one edge of the backing layer, the dressing having a fold in a direction parallel to the handling means with the backing layer on the outside of the fold and means releasably attaching a portion of the dressing beyond the fold to a portion of the dressing before the fold, the protector extending beyond the edge of the backing film at the edge opposite the handling means, and wherein the extended portion of the protector is folded so that a portion of its release coated surface contacts an adhesive surface of the means releasably attaching the portion of the dressing beyond the fold to the portion of the dressing before the fold.

2. An adhesive dressing according to claim 1 in which the fold is from 50 to 80% of the distance across the dressing measured from the edge of the dressing attached to the handling means.

3. An adhesive dressing according to claim 1 wherein said means releasably attaching a portion of the dressing beyond the fold to a portion of the dressing before the fold comprises a tape which has a coating of adhesive on either side.

4. An adhesive dressing according to claim 1 wherein said means releasably attaching a portion of the dressing beyond the fold to a portion of the dressing before the fold comprises a tape coated on only one surface with adhesive which is folded.

5. An adhesive dressing according to claim 1 wherein said means releasably attaching a portion of the dressing beyond the fold to a portion of the dressing before the fold comprises an adhesive strip.

6. An adhesive dressing according to claim 1 in which the protector is a single sided release paper comprising a silicone release/polyethylene coated paper.

7. An adhesive dressing according to claim 1 in which the b backing layer comprises a flexible polymer film formed from a polymer selected from the group consisting of polyurethane, polyether, polyester and polyamide-polyether.

8. An adhesive dressing according to claim 1 in which the adhesive layer comprises an acrylate ester copolymer adhesive or a polyvinyl alkyl ether adhesive applied at a weight per unit area of 10 to 75 gm$^{-2}$.

9. An adhesive dressing according to claim 8 in which the adhesive layer on the backing layer is continous and the adhesive coated backing layer has a moisture vapor transmission rate of at least 300 gm$^{-2}$ 24 h$^{-1}$ at 37° C. and 100% to 10% relative humidity difference.

10. An adhesive dressing according to claim 9 in which the adhesive contains from 1 to 10% by weight of the adhesive of antibacterial agent.

11. An adhesive dressing according to claim 1 in which the handling means comprises an adhesive coated net.

12. An adhesive dressing according to claim 1 in which the dressing is sterile and is packaged within a bacterial-proof pack.

13. A method of treating a patient by applying thereto an adhesive dressing comprising a backing layer having over one surface thereof a pressure sensitive adhesive layer, a removable protector having a release coated surface which covers the adhesive layer and handling means at one edge of the backing layer, the dressing having a fold in a direction parallel to the handling means with the backing layer on the outside of the fold and means releasably attaching a portion of the dressing beyond the fold to a portion of the dressing before the fold the protector extending beyond the edge of the backing film at the edge opposite the handling means, and wherein the extended portion of the protector is folded so that a portion of its release coated surface contacts an adhesive surface of the means releasably attaching the portion of the dressing beyond the fold to the portion of the dressing before the fold, which method comprises peeling the protector from the adhesive layer up to the fold, applying the adhesive surface to the skin and then peeling off the remainder of the protector.

14. A method according to claim 13 in which the fold is from 50 to 80% of the distance across the dressing measured from the edge of the dressing attached to the handling means.

15. A method according to claim 13 wherein said means releasably attaching a portion of the dressing beyond the fold to a portion of the dressing before the fold comprises a tape which has a coating of adhesive on either side.

16. A method according to claim 13 wherein said means releasably attaching a portion of the dressing beyond the fold to a portion of the dressing before the fold comprises a tape coated on only one surface with adhesive which is folded.

17. A method according to claim 13 wherein said means releasably attaching a portion of the dressing beyond the fold to a portion of the dressing before the fold comprises an adhesive strip.

18. A method according to claim 3 in which the protector is a single sided release paper comprising a silicone release/polyethylene coated paper.

19. A method according to claim 13 in which the backing layer comprises a flexible polymer film formed from a polymer selected from the group consisting of polyurethane, polyether, polyester and polyamide-polyether.

20. A method according to claim 13 in which the adhesive layer comprises an acrylate ester copolymer adhesive or a polyvinyl alkyl ether adhesive applied at a weight per unit area of 10 to 75 gm$^{-2}$.

21. A method according to claim 20 in which the adhesive layer on the backing layer is continuous and the adhesive coated backing layer has a moisture vapor transmission rate of at least 300 gm$^{-2}$ 24 h$^{-1}$ at 37° C. and 100% to 10% relative humidity difference.

22. A method according to claim 21 in which the adhesive contains from 1 to 10% by weight of the adhesive of antibacterial agent.

23. A method according to claim 13 in which the handling means comprises an adhesive coated net.

24. A method according to claim 13 in which the dressing is sterile and is packaged within a bacterial-proof pack.

25. A method of retaining an indwelling catheter on the body of a patient by employing an adhesive dressing which comprises a backing layer having over one surface thereof a pressure sensitive adhesive layer, a removable protector having a release coated surface which covers the adhesive layer and handling means at one edge of the backing layer, the dressing having a fold in a direction parallel to the handling means with the backing layer on the outside of the fold and means releasably attaching a portion of the dressing beyond the fold to a portion of the dressing before the fold the protector extending beyond the edge of the backing film at the edge opposite the handling means, and wherein the extended portion of the protector is folded so that a portion of its release coated surface contacts an adhesive surface of the means releasably attaching the portion of the dressing beyond the fold to the portion of the dressing before the fold, which method comprises peeling the protector from the adhesive layer up to the fold, applying the exposed adhesive surface to the skin surrounding the catheter and then peeling off the remainder of the protector.

26. A method according to claim 25 in which the fold is from 50 to 80% of the distance across the dressing measured from the edge of the dressing attached to the handling means.

27. A method according to claim 25 wherein said means releasably attaching a portion of the dressing beyond the fold to a portion of the dressing before the fold comprises a tape which has a coating of adhesive on either side.

28. A method according to claim 25 wherein said means releasably attaching a portion of the dressing beyond the fold to a portion of the dressing before the fold comprises a tape coated on only one surface with adhesive which is folded.

29. A method according to claim 25 wherein said means releasably attaching a portion of the dressing beyond the fold to a portion of the dressing before the fold comprises an adhesive strip.

30. A method according to claim 25 in which the protector is a single sided release paper comprising a silicone release/polyethylene coated paper.

31. A method according to claim 25 in which the backing layer comprises a flexible polymer film formed from a polymer selected from the group consisting of polyurethane, polyether, polyester and polyamide-polyether.

32. A method according to claim 25 in which the adhesive layer comprises an acrylate ester copolymer adhesive or a polyvinyl alkyl ether adhesive applied at a weight per unit area of 10 to 75 $gm^{-2}$.

33. A method according to claim 32 in which the adhesive layer on the backing layer is continuous and the adhesive coated backing layer has a moisture vapor transmission rate of at least 300 $gm^{-2}$ 24 $h^{-1}$ at 37° C. and 100% to 10% relative humidity difference.

34. A method according to claim 33 in which the adhesive contains from 1 to 10% by weight of the adhesive of antibacterial agent.

35. A method according to claim 25 in which the handling means comprises an adhesive coated net.

36. A method according to claim 25 in which the dressing is sterile and is packaged within a bacterial-proof pack.

* * * * *